United States Patent
DeLuca

Patent Number: 5,981,780
Date of Patent: Nov. 9, 1999

[54] 19-NOR-VITAMIN $D_3$ COMPOUNDS WITH CALCEMIC ACTIVITY

[75] Inventor: Hector F. DeLuca, Deerfield, Wis.

[73] Assignee: Wisconsin Alumni Research Foundation, Madison, Wis.

[21] Appl. No.: 09/311,403

[22] Filed: May 13, 1999

Related U.S. Application Data

[62] Division of application No. 09/135,947, Aug. 18, 1998.

[51] Int. Cl.[6] .......................... C07C 401/00; A61K 31/59
[52] U.S. Cl. ............................................ 552/653; 514/167
[58] Field of Search .............................. 552/653; 514/167

[56] References Cited

U.S. PATENT DOCUMENTS

| | | | |
|---|---|---|---|
| 4,847,012 | 7/1989 | DeLuca et al. | 260/397 |
| 4,851,401 | 7/1989 | DeLuca et al. | 514/167 |
| 5,086,191 | 2/1992 | DeLuca et al. | 552/653 |
| 5,281,731 | 1/1994 | DeLuca et al. | 552/653 |
| 5,393,749 | 2/1995 | DeLuca et al. | 514/167 |
| 5,587,497 | 12/1996 | DeLuca et al. | 552/653 |

FOREIGN PATENT DOCUMENTS

WO 90/09991  9/1990  WIPO.
WO 95/01960  1/1995  WIPO.

OTHER PUBLICATIONS

Perlman et al, "Novel Synthesis of 19–Nor–Vitamin D Compounds," Tetrahedron Letters, vol. 52, No. 52, pp. 7663–7666, 1991.

Perlman et al, "1α,25–Dihydroxy–19–Nor–Vitamin $D_3$, A Novel Vitamin D–Related Compound with Potential Therapeutic Activity," Tetrahedron Letters, vol. 31, No. 13, pp. 1823–1824, 1990.

Primary Examiner—S. Mark Clardy
Assistant Examiner—Sabiha N. Qazi
Attorney, Agent, or Firm—Andrus, Sceales, Starke & Sawall

[57] ABSTRACT

The 26 and/or 27 homologated analogs of 19-nor-1α,25-dihydroxyvitamin $D_3$ are disclosed as having relatively high calcemic activity. The 26 and/or 27 homologated analogs showed strong in vivo calcium transport as well as bone calcium mobilization activity. These analogs also induced differentiation of malignant cells. These analogs thus show promise in the treatment of osteoporosis, and a possible use in the treatment of cancerous diseases.

3 Claims, 2 Drawing Sheets

19-NOR-VITAMIN $D_3$ COMPOUNDS WITH CALCEMIC ACTIVITY

CROSS-REFERENCE TO RELATED APPLICATIONS

This application is a division of application Ser. No. 09/135,947 filed Aug. 18, 1998.

STATEMENT REGARDING FEDERALLY SPONSERED RESEARCH OR DEVELOPMENT

This invention was made with United States Government support awarded by the National Institutes of Health (NIH), Grant #DK-14881. The United States Government has certain rights in this invention.

BACKGROUND AND SUMMARY OF THE INVENTION

This invention relates to biologically active vitamin $D_3$ compounds. More specifically, the invention relates to 19-nor-analogs of 1α-hydroxylated vitamin $D_3$ compounds having calcemic activity.

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans, and their activity in cellular differentiation has also been established. V. Ostrem et al, Proc. Natl. Acad. Sci. USA, (1987), 84, 2610. As a consequence, many structural analogs of these metabolites, such as compounds with different side chain structures, different hydroxylation patterns, or different stereochemistry, have been prepared and tested. Important examples of such analogs are 1α-hydroxyvitamin $D_3$, 1α-hydroxyvitamin $D_2$, various side chain fluorinated derivatives of 1α, 25-dihydroxyvitamin $D_3$, and side chain homologated analogs. Several of these known compounds exhibit highly potent activity in vivo or in vitro and some of these have been found to exhibit an interesting separation of activities in cell differentiation and calcium regulation. This difference in activity provides these compounds with advantageous therapeutic activity profiles and thus numerous of these compounds are in use, or have been proposed for use, in the treatment of a variety of diseases such as renal osteodystrophy, vitamin D-resistant rickets, osteoporosis, psoriasis, and certain malignancies.

Recently, a new class of vitamin D analogs has been discovered, i.e. the so-called 19-nor-vitamin D compounds. 19-Nor-vitamin D compounds are vitamin D analogs in which the ring A exocyclic methylene group (carbon 19) typical of all vitamin D compounds has been removed and replaced by two hydrogen atoms. Specifically, these compounds were reported to exhibit a selective activity profile with high potency in inducing cellular differentiation, and minimal bone calcification activity. See U.S. Pat. No. 5,587, 497. Such a differential activity profile renders these compounds useful for the treatment of malignancies, or the treatment of various skin disorders such as psoriasis. Several different methods of synthesis of these 19-nor-vitamin D analogs have been described (Perlman et al. Tetrahedron Letters 31, 1823 (1990); Perlman et al Tetrahedron Letters 32, 7663 (1991); and DeLuca et al U.S. Pat. No. 5,086,191).

In a continuing effort to explore the new 19-nor class of pharmacologically important vitamin D analogs, the 19-nor-26,27-dihomo-1α,25-$(OH)_2D_3$ and the 19-nor-26,27-dihomo-22,23(E)-1α,25-$(OH)_2D_3$ analogs of 19-nor-1α,25-dihydroxyvitamin $D_3$ have now been synthesized. The two 26,27 homologated analogs showed relatively high in vivo calcemic activity, i.e. calcium transport activity and bone calcium mobilization activity. Both analogs also induced differentiation of HL-60 cells. These two analogs as well as other 26 and/or 27 homologated 19-nor compounds disclosed hereinafter thus show promise in the treatment of osteoporosis.

DETAILED DESCRIPTION OF THE INVENTION

Figure 1:
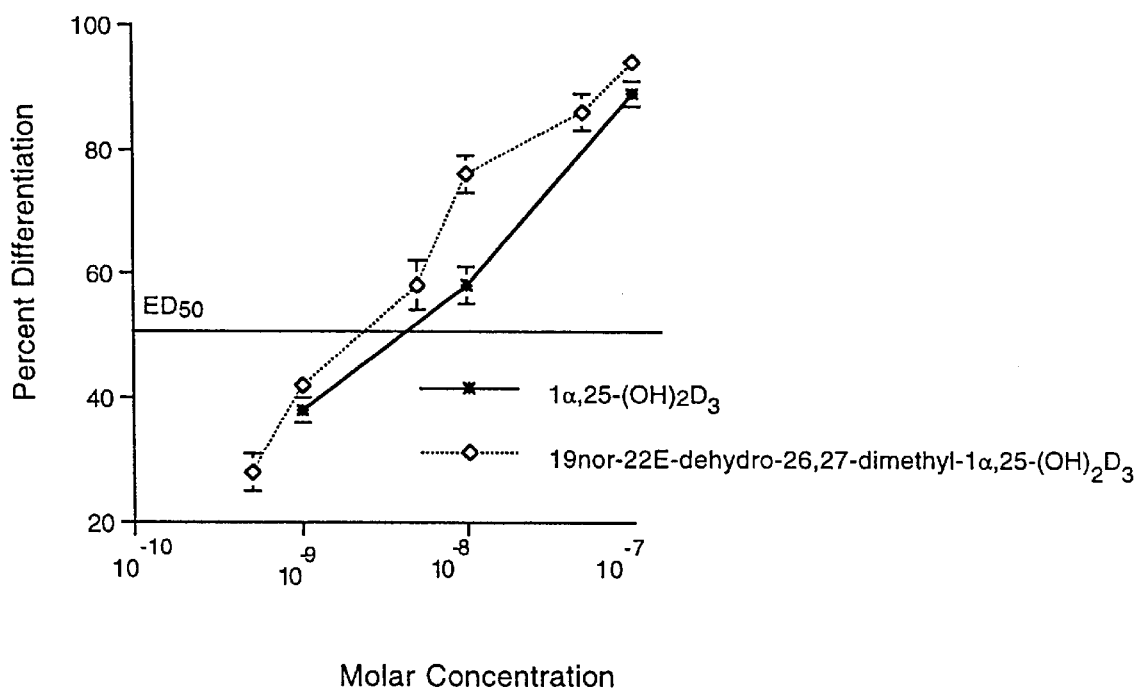
FIG. 1 is a graph of the percent differentiation of HL-60 cells versus concentration of 1α,25-$(OH)_2D_3$ as compared to 19-nor-26,27-dimethyl-22,23(E)-1α,25-$(OH)_2D_3$.

The 26 and/or 27-homologated 19-nor-Vitamin $D_3$ analogs that are useful in the treatment of osteoporosis are represented by the following general formula:

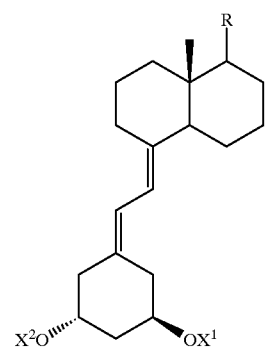

I where $X^1$ and $X^2$, which may be the same or different, are each selected from hydrogen and a hydroxy protecting group, and where the group R represents any of the typical side chains known for vitamin D type compounds that are, in addition, homologated at the carbon 26 and/or 27 positions. More specifically, R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups that are, in addition, homologated at the carbon 26 and/or 27 positions. Preferred side chains of this type are represented by the structure below:

where the stereochemical center (corresponding to C-20 in steroid numbering) may have the R or S configuration, (i.e. either the natural configuration about carbon 20 or the 20-epi configuration), and where Z is selected from Y, —OY, —$CH_2OY$, —C≡CHY, and —CH=CHY where the double bond may have the cis or trans geometry, and where Y is selected from a radical of the structure:

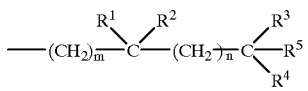

where m and n, independently, represent the integers from 0 to 5, where each of $R^1$ and $R^2$, independently, is selected from hydrogen, deuterium, deuteroalkyl, hydroxy, protected hydroxy, fluoro, trifluoromethyl, and $C_{1-5}$-alkyl, which may be straight chain or branched and, optionally, bear a hydroxy or protected-hydroxy substituent, and where each of $R^3$ and $R^4$, independently, is selected from $C_{2-5}$ alkyl, which may be straight-chain or branched, and optionally, bear a hydroxy or protected-hydroxy substituent, and where $R^1$ and $R^2$, taken together, represent an oxo group, or an alkylidene group, $=CR^2R^3$, or the group —$(CH_2)_p$—, where p is an integer from 2 to 5, and where $R^3$ and $R^4$, taken together, represent the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22 or 23 in the side chain may be replaced by a nitrogen atom, or where any of the groups —CH(CH$_3$)—, —CH$_2$—, or —CH(R$^2$)— at positions 20, 22, and 23, respectively, may be replaced by an oxygen or sulfur atom.

Specific important examples of side chains are the structures represented by formulas (a), (b), (c), (d) and (e) below where $R^3$ and $R^4$ are as defined above.

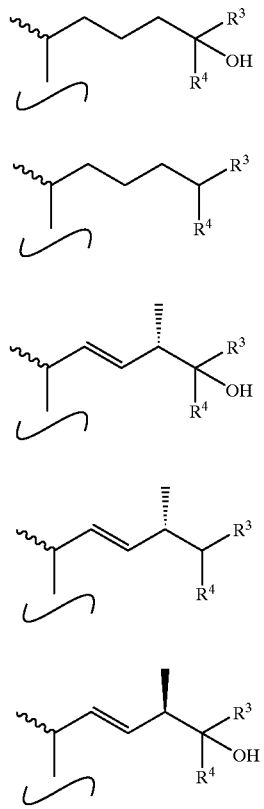

These 19-nor-vitamin D compounds are characterized by homologation at the 26 and/or 27 positions since $R^3$ and $R^4$ are each defined as $C_{2-5}$ alkyl. It should be noted that with respect to all homologated compounds, whether the compound is 26 and/or 27 homologated, the above-noted structural formula encompasses 25-hydroxylated compounds, 1α-hydroxylated compounds, as well as 1α-25-dihydroxylated compounds.

Specific, and preferred, side chains are the following structures (f), (g), (h), (i), (j) ) and (k):

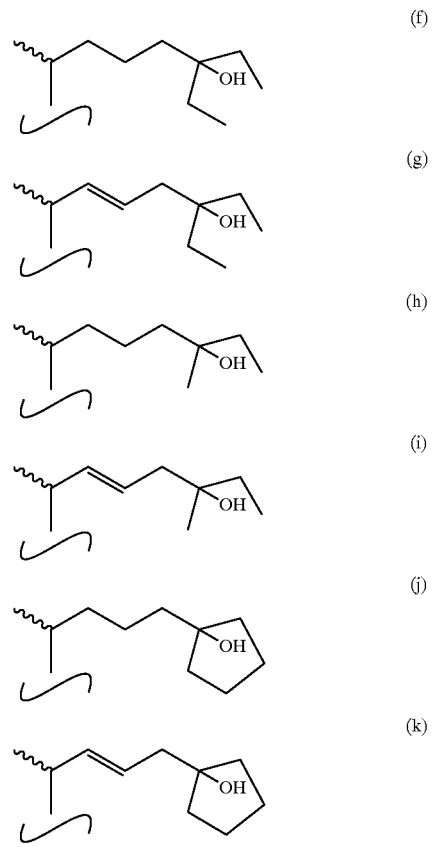

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl—O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms, such as methyl, ethyl, propyl, isopropyl, butyl, isobutyl, pentyl, etc. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "26-homo" or "27-homo" refers to the addition of one methylene group and the term "26-dihomo" or "27-dihomo" refers to the addition of two methylene groups at the carbon 26 or 27 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa", "22-oxa" or "23-oxa", respectively, should be added to the named compound. The named compounds could also be of the vitamin $D_2$ type if desired.

Specific and preferred examples of the 19-nor-26 and/or 27 homologated compounds of structure I when the side chain is unsaturated are:

19-nor-26,27,dimethyl-1,25-dihydroxy-22,23-dehydrovitamin $D_3$;
19-nor-26,27-diethyl-1,25-dihydroxy-22,23-dehydrovitamin $D_3$;
19-nor-26,27-dipropoyl-1,25-dihydroxy-22,23-dehydrovitamin $D_3$;
19-nor-26,27-dimethyl-24-homo-1,25-dihydroxy-22,23-dehydrovitamin $D_3$;
19-nor-26,27-dimethyl-24-dihomo-1,25-dihydroxy-22,23-dehydrovitamin $D_3$;
19-nor-26,27-dimethyl-24-trihomo-1,25-dihydroxy-22,23-dehydrovitamin $D_3$;
19-nor-26,27-diethyl-24-homo-1,25-dihydroxy-22,23-dehydrovitamin $D_3$;
19-nor-26,27-diethyl-24-dihomo-1,25-dihydroxy-22,23-dehydrovitamin $D_3$;
19-nor-26,27-diethyl-24-trihomo-1,25-dihydroxy-22,23-dehydrovitamin $D_3$;
19-nor-26,27-dipropoyl-24-homo-1,25-dihydroxy-22,23-dehydrovitamin $D_3$;
19-nor-26,27-dipropyl-24-dihomo-1,25-dihydroxy-22,23-dehydrovitamin $D_3$;
19-nor-26,27-dipropyl-24-trihomo-1,25-dihydroxy-22,23-dehydrovitamin $D_3$;
19-nor-26,27-dimethylene-1,25-dihydroxy-22,23-dehydrovitamin $D_3$; and
19-nor-26,27-dimethylene-24-epi-1,25-dihydroxy-22,23-dehydrovitamin $D_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" should be included in each of the above named compounds. Also, it is common to designate the double bond located between the 22 and 23 carbon atoms with the designation "$\Delta^{22}$". Thus, for example, the first named compound above could also be written as 19-nor-26,27-dimethyl-22,23(E)-$\Delta^{22}$-1,25-(OH)$_2D_3$ where the double bond is in the (E) configuration. Similarly, if the methyl group attached at carbon 20 is in the unnatural configuration, this compound could be written as 19-nor-20(S)-26,27-dimethyl-22,23(E)-$\Delta^{22}$-1,25-(OH)$_2D_3$.

Specific and preferred examples of the 19-nor-26 and/or 27 homologated compounds of structure I when the side chain is saturated are:

19-nor-26,27-dimethyl-1,25-dihydroxyvitamin $D_3$;
19-nor-26,27-diethyl-1,25-dihydroxyvitamin $D_3$;
19-nor-26,27-dipropyl-1,25-dihydroxyvitamin $D_3$;
19-nor-26,27-dimethyl-24-homo-1,25-dihydroxyvitamin $D_3$;
19-nor-26,27-dimethyl-24-dihomo-1,25-dihydroxyvitamin $D_3$;
19-nor-26,27-dimethyl-24-trihomo-1,25-dihydroxyvitamin $D_3$;
19-nor-26,27-diethyl-24-homo-1,25-dihydroxyvitamin $D_3$;
19-nor-26,27-diethyl-24-dihomo-1,25-dihydroxyvitamin $D_3$;
19-nor-26,27-diethyl-24-trihomo-1,25-dihydroxyvitamin $D_3$;
19-nor-26,27-dipropyl-24-homo-1,25-dihydroxyvitamin $D_3$;
19-nor-26,27-dipropyl-24-dihomo-1,25-dihydroxyvitamin $D_3$;
19-nor-26,27-dipropyl-24-trihomo-1,25-dihydroxyvitamin $D_3$;
19-nor-26,27-dimethylene-1,25-dihydroxyvitamin $D_3$; and
19-nor-26,27-dimethylene-24-epi-1,25-dihydroxyvitamin $D_3$.

The preparation of 19-nor-vitamin D compounds having the structure shown above can be accomplished by any of several different common general methods using known starting materials. Suitable methods are illustrated and described in U.S. Pat. Nos. 5,587,497; 5,281,731; 5,086,191; 4,851,401; and 4,847,012, the descriptions of which are specifically incorporated herein by reference.

Methods of synthesis of these 19-nor-vitamin D analogs have also been described in Perlman et al, Tetrahedron Letters 31, 1823 (1990), and Perlman et al, Tetrahedron Letters 32, 7663 (1991).

A number of oxa-analogs of vitamin $D_3$ and their synthesis are also known. For example, 20-oxa analogs are described in N. Kubodera et al, Chem. Pharm. Bull., 34, 2286 (1986), and Abe et al, FEBS Lett. 222, 58, 1987. Several 22-oxa analogs are described in E. Murayama et al, Chem. Pharm. Bull., 34, 4410 (1986), Abe et al, FEBS Lett., 226, 58 (1987), PCT International Application No. WO 90/09991 and European Patent Application, publication number 184 112, and a 23-oxa analog is described in European Patent Application, publication number 78704, as well as U.S. Pat. No. 4,772,433.

Biological Activity of 1α-Hydroxy-19-Nor-26 and/or 27 Homologated Vitamin D Compounds The compounds of this invention exhibit an unexpected pattern of biological activity. 19-nor-26,27-dimethyl-1α,25-dihydroxy-22,23(E)-dehydrovitamin $D_3$ exhibited high binding activity to the porcine intestinal vitamin D receptor, and high potency in promoting the differentiation of malignant cells. These two activities were essentially equivalent to the natural hormone 1α,25-(OH)$_2$D$_3$ (See FIGS. 1 and 2). In addition, the 19-nor-26,27-dimethyl-1,25-(OH)$_2$D$_3$ analog showed a selective calcemic activity profile, combining high potency in inducing intestinal calcium transport with very high bone mobilizing activity. The above is illustrated by the biological assay results obtained for the tested 19-nor-vitamin D$_3$ compounds, which are summarized in FIGS. 1 and 2, and Table 1.

EXAMPLE 1

FIG. 1 shows a comparison of the activity of the known active metabolite 1α,25-dihydroxyvitamin D$_3$ and the 19-nor-26,27-dimethyl-22,23(E)-dehydrovitamin D$_3$ analog in inducing the differentiation of human leukemia cells (HL-60 cells) in culture to normal cells (monocytes). Differentiation activity was assessed by a standard differentiation assay, abbreviated in FIG. 1 as NBT (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to normal cells in response to a given concentration of test compound.

The results summarized in FIG. 1 clearly show that the 19-nor-26,27-dimethyl-22,23(E)-dehydrovitamin D$_3$ analog is as potent as 1α,25-dihydroxyvitamin D$_3$ in promoting the differentiation of leukemia cells. Thus in NBT assay close to 90% of the cells are induced to differentiation by 1α,25-dihydroxyvitamin D$_3$ at a concentration of $1 \times 10^{-7}$ molar, and the same degree of differentiation is achieved by the 19-nor analog.

Figure 2:
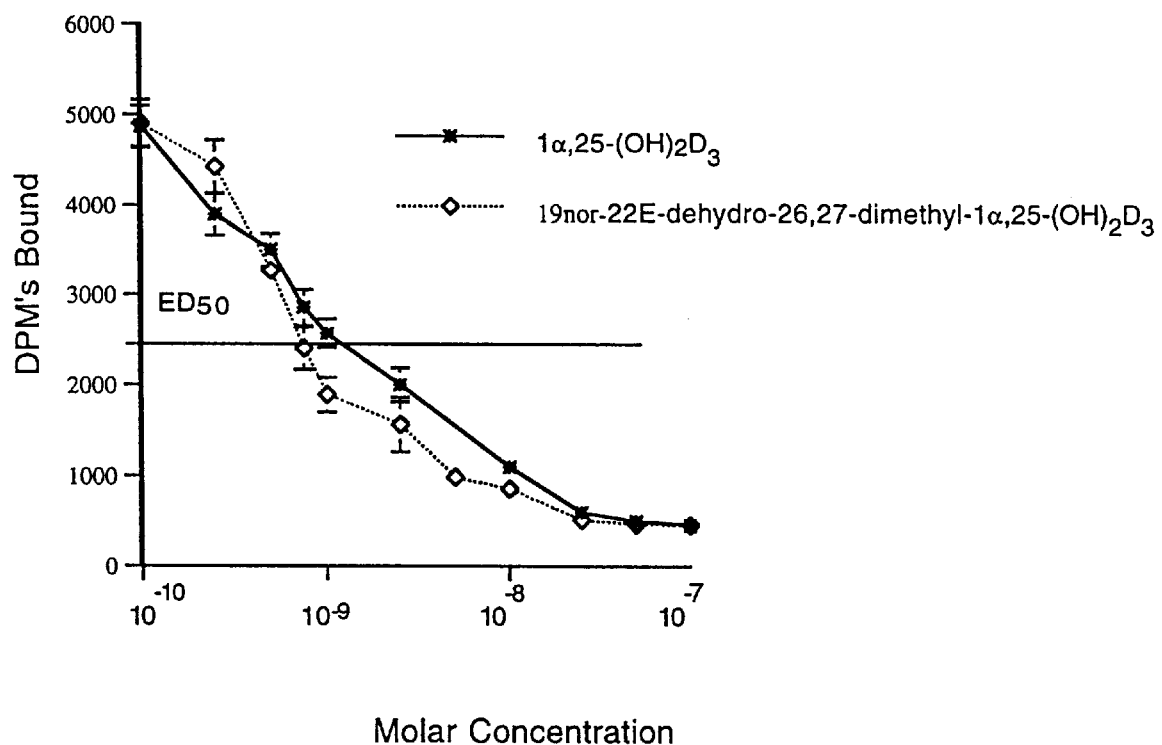
FIG. 2 is a graph of the competitive binding ability versus concentration for the same two compounds as in FIG. 1.

FIG. 2 shows a comparison of the same two compounds as in FIG. 1 illustrating their relative activity with regard to competitive binding to the vitamin D receptor. The competitive receptor binding was done with pig nuclear extract as described in Perlman et al. Biochemistry 29, 190–196 (1990) using the porcine extract prepared as described by Dame et al PNAS 82, 7825–7829 (1985). These data are used to demonstrate that the compounds described herein have relatively high in vivo activity, and have somewhat less activity than 1,25-(OH)$_2$D$_3$ in binding to the vitamin D receptor.

EXAMPLE 2

The biological data on the calcemic activity of the compound 19-nor-26,27-dimethyl-1α,25-(OH)$_2$D$_3$ is reported in Table 1. In this study Holtzmann weanling rats were maintained on a low Ca diet (0.02% Ca, 0.3% P) for three weeks. During the 4th week all animals were dosed with the appropriate compounds via the peritonal cavity. All doses were suspended in ethanol propylene glycol (5/95) and administered daily for seven days. None of the compounds produced hypercalcemia over the seven day dosing period.

The data in Table 1 illustrate that 19-nor-26,27-dimethyl-1α,25-dihydroxyvitamin D$_3$ has biological activity in intestinal calcium transport similar to that of 1,25-(OH)$_2$D$_3$ and possesses bone calcium mobilizing activity greater than 1,25-(OH)$_3$D$_3$. Thus, the 19-nor-26,27-dimethyl-1α,25-dihydroxyvitamin D$_3$ compound has an activity profile similar to 1,25-(OH)$_2$D$_3$ but has preferential activity on bone.

TABLE 1

Response of Intestinal Calcium Transport and Serum Calcium (Bone Calcium Mobilization) Activity to Chronic Doses of the 26,27-Dimethyl Derivative of 19-Nor-1,25-(OH)$_2$D$_3$

| Group | Dose (pmol/day/7 days) | Intestinal Calcium Transport (S/M) | Serum Calcium (mg/100 ml) |
|---|---|---|---|
| Vitamin D Deficient | Vehicle | 4.5 ± 0.09 | 4.5 ± 0.1 |
| 1,25-(OH)$_2$D$_3$ Treated | 0.1 | 10.0 ± 0.98 | 6.0 ± 0.13 |
| 19-Nor-26,27-Dimethyl-1,25-(OH)$_2$D$_3$ | 0.1 | 8.3 ± 0.85 | 8.0 ± 0.23 |
|  | 1.0 | 9.1 ± 1.1 | 8.9 ± 0.21 |
|  | 10.0 | 9.3 ± 0.33 | 10.0 ± 0.42 |

EXAMPLE 3

This experiment and the data in Table 2 show very clearly that the two compounds tested are extremely effective in increasing bone mass of ovariectomized animals.

This experiment was carried out with 8-month-old female rats purchased from Sprague-Dawley Company. 88 of the 100 rats were ovariectomized; the other 12 were sham operated. They were fed the Purina Rat Chow diet 5012 ad libitum and distilled water throughout the entire experiment. The sham-operated and ovariectomized rats were allowed to proceed with monitoring by the DPXα of Lunar Corporation that measures whole animal bone mineral density. It took 5 months of depletion before significant difference could be found in bone mineral density of the ovariectomized versus sham-operated controls. At this point, the sham-operated controls were allowed to continue as before, while the ovariectomized animals were divided into groups of 12 animals per group. They were given the indicated doses for a period of 7 months. Bone densities were measured at 7 months, at 10 months, and at 12 months. The animals were sacrificed at that point, femurs were removed to determine total and percent ash, and plasma was taken for the determination of serum calcium concentration. The results are provided as the mean±standard error of the means for 12 animals. Bone density was determined by dual photon absorptiometry as indicated from the manual for the DPXα instrument of Lunar Corporation. There is also a reference to the calculations that are made from the absorption of photons by the skeleton. This is supplemented with the chemical determination of the ash content in mg. Percent ash is also reported to indicate that there was no osteomalacia but rather only osteoporosis was being treated.

The results in Table 2 show very clearly that ovariectomy caused a major loss of bone mineral of about 120 mg per femure. The 19-nor-26,27-dimethyl-22,23(E)-Δ$^{22}$-1,25-(OH)$_2$D$_3$ gave the largest increase in ash content of the femur, largest bone mineral density increase and the largest bone mineral content. These animals were not hypercalcemic as judged by the controls on the same diet. Less dramatic increases were registered by the 19-nor-20(S)-26, 27-dimethyl-22,23(E)-$\Delta^{22}$-1,25-(OH)$_2$D$_3$. The lower the dose, the less mineral accumulating in the femurs. However, even at 400 pmol/kg 3 times a week, a large increase above ovariectomy was demonstrated. It is important to note that only small increases in bone mineral were provided by 1,25-(OH)$_2$D$_3$ under the same conditions. These results illustrate very clearly that the 19-nor-26,27-dimethyl compounds are superior to 1,25-(OH)$_2$D$_3$ in increasing bone mineral content, ash content of bone, and bone mineral density. At 600 pmol/kg 3 times a week, the 19-nor-26,27-dimethyl-22,23(E)-$\Delta^{22}$-1,25-(OH)$_2$D$_3$ gave ash values in excess of sham-operated controls, illustrating that not only did it restore the mineral that had been lost because of ovariectomy, but actually increased it above sham-operated control values. These results support the use of these compounds for the treatment of osteoporosis in general and post-menopausal osteoporosis in particular.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention. Due to their high calcium activity, these compounds can also be used to treat hypocalcemic diseases such as hypoparathyroidism.

The above 19-nor compounds are also characterized by high cell differentiation activity. Thus, these compounds also provide therapeutic agents for the treatment of psoriasis, or as an anti-cancer agent, especially against leukemia, colon cancer, breast cancer and prostate cancer. The compounds may be present in a composition to treat psoriasis in an

TABLE 2

RESTORATION OF BONE IN OVARIECTOMIZED RATS BY 19-NOR-26,27-DIMETHYL-22,23(E)-$\Delta^{22}$-1,25-DIHYDROXYVITAMIN D$_3$ AND ITS 20S ISOMER

| Group | Dose | Bone Mineral Density (g/cm$^2$) | Bone Mineral Content (grams) | Bone Ash mg/femur % | | Serum Calcium (mg/100 ml) |
|---|---|---|---|---|---|---|
| Ovariectomy | 0 | 0.297 ± 0.004 | 8.875 ± 0.488 | 396 ± 17 | 56 ± 0.1 | 11.0 ± 0.21 |
| Sham | 0 | 0.329 ± 0.002 | 11.814 ± 0.417 | 514 ± 18 | 60 ± 0.6 | 10.9 ± 0.4 |
| 19-nor-26,27-dimethyl-22,23(E)-$\Delta^{22}$,1,25-(OH)$_2$D$_3$ | 600 pmol/kg 2× week | 0.346 ± 0.005 | 13.548 ± 0.384 | 569 ± 8.8 | 62 ± 0.3 | 11.7 ± 0.3 |
| | 400 pmol/kg 2× week | 0.322 ± 0.019 | 10.837 ± 0.643 | 458 ± 24 | 60 ± 0.6 | 11.2 ± 0.18 |
| 19-nor-20(S)-26,27-dimethyl-22,23(E)-$\Delta^{22}$,1,25-(OH)$_2$D$_3$ | 600 pmol/kg 3× week | 0.326 ± 0.007 | 11.456 ± 0.724 | 476 ± 34 | 60 ± 0.8 | 11.9 ± 0.1 |
| | 400 pmol/kg 3× week | 0.322 ± 0.004 | 10.655 ± 0.306 | 451 ± 12 | 60 ± 0.24 | 12.0 ± 0.2 |
| 1,25-(OH)$_2$D$_3$ | 400 pmol/kg 3× week | 0.304 ± 0.003 | 10.211 ± 0.5 | 432 ± 17 | 56 ± 1.00 | 10.3 ± 0.13 |
| | 200 pmol/kg 3× week | 0.306 ± 0.003 | 10.09 ± 0.58 | 422 ± 18 | 58 ± 0.6 | 10.2 ± 0.16 |

The above 19-nor compounds thus exhibit a desired, and highly advantageous, pattern of biological activity. These compounds are characterized by relatively high intestinal calcium transport activity, but less than that of 1α,25-dihydroxyvitamin D$_3$, while also exhibiting much higher bone calcium mobilizing activity. Hence, these compounds are highly specific in their calcemic activity. Their preferential activity on mobilizing calcium from bone and intestinal calcium transport activity allows the in vivo administration of these compounds for the treatment of metabolic bone diseases where bone loss is a major concern. Because of their preferential calcemic activity on bone, these compounds would be preferred therapeutic agents for the treatment of diseases where bone formation is desired, such as osteoporosis, especially low bone turnover osteoporosis, steroid induced osteoporosis, senile osteoporosis or post-menopausal osteoporosis, as well as osteomalacia and renal osteodystrophy. The treatment may be transdermal, oral, sublingual, intranasal or parenteral. The compounds may be present in a composition in an amount from about 0.1 μg/gm to about 50 μg/gm of the composition, and may be administered in dosages of from about 0.1 μg/day to about 50 μg/day.

amount from about 0.01 μg/gm to about 100 μg/gm of the composition, and may be administered topically, transdermally, orally, sublingually, intranasally, or parenterally in dosages of from about 0.01 μg/day to about 100 μg/day.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally, sublingually, intranasally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 μg to 50 μg per day of the compounds are appropriate for treatment purposes, such doses being adjusted according to the disease to be treated, its severity and the response of the subject as is well understood in the art. Since the compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of one or more 26 and/or 27 homologated-19-nor-vitamin D compound as defined by the above formula I as the active ingredient, and a suitable carrier. An effective amount of such compounds for use in accordance with this invention is from about 0.01 μg to about 100 μg per gm of composition, and may be administered topically, transdermally, orally, sublingually, intranasally, or parenterally in dosages of from about 0.1 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

I claim:

1. 19-nor-26,27-dimethyl-1α,25-dihydroxyvitamin $D_3$.
2. 19-nor-26,27-dimethyl-1α,25-dihydroxy-22,23(E)-dehydrovitamin $D_3$.
3. 19-nor-20(S)-26,27-dimethyl-1α,25-dihydroxy-22,23(E)-dehydrovitamin $D_3$.

* * * * *